US005759535A

United States Patent [19]
Cohen

[11] Patent Number: 5,759,535
[45] Date of Patent: Jun. 2, 1998

[54] IMMUNOTHERAPEUTIC STRATEGIES FOR THE TREATMENT OF CANCER

[75] Inventor: Edward P. Cohen. Chicago, Ill.

[73] Assignee: Research Corporation Technologies, Inc., Tucson, Ariz.

[21] Appl. No.: 242,405

[22] Filed: May 13, 1994

[51] Int. Cl.⁶ .................................................. A61K 48/00
[52] U.S. Cl. .............................. 424/93.21; 435/172.3; 435/69.1; 435/320.1
[58] Field of Search .................... 514/44, 2; 435/172.3, 435/172.1, 240.1, 240.2, 320.1, 91.1; 424/93.21; 536/22.1, 23.1, 24.1

[56] References Cited

U.S. PATENT DOCUMENTS 5,674,486  10/1997  Sobol et al. ....................... 424/93.21

FOREIGN PATENT DOCUMENTS 9307906  11/1993  WIPO .

OTHER PUBLICATIONS

Ostrand–Rosenberg et al, Tumor Specific Immunity . . . , Int. J. Cancer. Supp. 6, 61–68 (1991.
Marshall, Science, 269:1050–1055, 1995.
Miller et al., FASEB J., 9:190–199, 1995.
Calver et al., TIG, 10(5): 174–179, 1994.
Hodgson, Exp. Opin. Ther. Pat., 5(5):459–468, 1995.
Nih "Report and Recommendations . . . ". Dec. 7, 1995, 1–40.
Blankenstein, T. et al., Tumor Suppression after Tumor Cell–targeted Tumor Necrosis Factor α Gene Transfer, J. Exp. Med., 173: 1047–1052 (1991).
Colombu. M. et al., Granulocyte Colony–stimulating Factor Gene Transfer Suppresses Tumorigenicity of a Murine Adenocarcinoma In Vivo, J. Exp. Med., 173: 889–897 (1991).
Dranoff, G. et al., Vaccination with irradiated tumor cells engineered to secrete murine granulocyte–macrophage colony–stimulating factor stimulates potent, specific, and long-lasting anti-tumor immunity, Proc. Natl. Acad. Sci. USA, 90: 3539–3543 (1993).
Fearon, E.R. et al., Interleukin–2 Production by Tumor Cells Bypasses T Helper Function in the Generation of an Antitumor Response, Cell, 60: 397–403 (1990).
Ferrantini, M. et al., αI–Interferon Gene Transfer into Metastatic Friend Leukemia Cells Abrogated Tumorigenicity in Immunocompetent Mice: Antitumor Therapy by Means of Interferon–producing Cells, Cancer Res., 53: 1107–1112 (1993).
Golumbek, P. et al., Treatment of Established Renal Cancer by Tumor Cells Engineered to Secrete Interleukin–4, Science, 254: 713–716 (1991).
Hui, K.M. et al., Tumor rejection mediated by transfection with allogeneic class I histocompatibility gene, J. Immunol., 143: 3825–3843 (1989).
Karp, S.E. et al., Cytokine Secretion by Genetically Modified Nonimmunogenic Murine Fibrosarcoma, J. Immunol., 150: 896–908 (1993).

Kim, T.S. et al., MHC antigen expression by melanomas recovered from mice treated with allogeneic mouse fibroblasts genetically modified for interleukin–2 secretion and the expression of melanoma–associated antigens, Cancer Immunol. Immunother., 38: 185–193 (1994).
Kim, T.S. et al., Independent pathways are involved in the induction of antimelanoma responses in C57BL/6 mice immunized with interleukin–2–secreting allogeneic mouse fibroblasts expressing melanoma associated antigens, J. Immunother., 14: 298–304 (1993).
Kim, T.S. et al., Immunization with interleukin–2–secreting allogeneic mouse fibroblasts expressiing melanoma assoicated antigens prolongs the survival of tumor–bearing mice, Int. J. Cancer, 55: 865–872 (1993).
Kim, T.S. et al., Immunity to B16 melanoma in mice immunized with IL–2–secreting allogeneic mouse fibroblasts expressing melanoma associated antigens, Int. J. Cancer, 51: 283–289 (1992).
Ostrand–Rosenberg, S. et al., Tumor–specific immunity can be enhanced by transfection of the tumor cells with syngeneic MHC class II genes or allogeneic MHC class I genes, Int. J. Cancer, 6(suppl.): 61–68 (1991).
Pardoll, D.M., Cancer vaccines, Immunol. Today, 14(6): 310–316 (1993).
Pardoll, D.M., New strategies for active immunotherapy with genetically engineered tumor cells, Curr. Opin. Immunol., 4: 619–623 (1992).
Porgador, A. et al., Antimetastatic Vaccination of Tumor–Bearing Mice with Two Types of IFN–γ Gene–Inserted Tumor Cells, J. Immunol., 150: 1458–1470 (1993).
Porgador, A. et al., Anti–metastatic vaccination of tumor–bearing mice with IL–2–gene–inserted tumor cells, Int. J. Cancer, 53: 471–477 (1993).
Porgador, A. et al., Interleukin 6 Gene Transfection into Lewis Lung Carcinoma Tumor Cells Suppresses the Malignant Phenotype and Confers Immunotherapeutic Competence against Parental Metastatic Cells, Cancer Res., 52: 3679–3686 (1992).
Rosenberg, S.A., The immunotherapy and gene therapy of cancer, J. Clin. Oncol., 10: 180–199 (1992).
Russell, S.J. et al., Decreased tumorigenicity of a transplantable sarcoma following transfer and expression of an IL–2 cDNA, Int. J. Cancer, 47: 244–251 (1991).
Weber, J.S. et al., Modulation of Murine Tumor Major Histocompatibility Antigens by Cytokines in Vivo and in vitro, Cancer Res., 48: 5818–5824 (1988).
Yamada, G. et al., Retroviral expression of the human IL–2 gene in a murine T cell line results in cell growth autonomy and tumorigenicity, EMBO J., 6: 2705–2709 (1987).
Zoller, M. et al., Interferon–Gamma Treatment of B16 Melanoma Cells: Opposing Effects for Non–Adaptive and Adaptive Immune Defense and its Reflection by Metastatic Spread, Int. J. Cancer, 41: 256–266 (1988).

Primary Examiner—Jasemine C. Chambers
Assistant Examiner—Karen M. Hauda
Attorney, Agent, or Firm—Scully, Scott, Murphy & Presser

[57] ABSTRACT

The present invention is directed to a method for the treatment of neoplastic disease comprising administering to a mammal having a tumor a cellular immunogen comprising an allogeneic population of cells expressing S one or more cytoldnes and tumor associated antigens encoded by autologous genomic tumor DNA.

14 Claims, 3 Drawing Sheets

IMMUNOTHERAPEUTIC STRATEGIES FOR THE TREATMENT OF CANCER

The government may own certain rights in the present invention pursuant to a grant from the National Institutes of Health CA55651-02.

BACKGROUND OF THE INVENTION

Most progressively growing neoplasms do not provoke immunological responses sufficient to control the growth of malignant cells despite the fact that the tumor cells express antigens which are recognizable as foreign by the immune system of the patient. (Sibille, C., et al., *J. Ex. Med.* 172:35–45[1990]).

Only recently have tumor-associated antigens (TAA), capable of being recognized by the cellular immune system (T-cells) been identified. These antigens (also referred to as tumor associated or T-cell epitopes) include oncogene products activated by mutation and rearrangement (e.g., position 12 mutation in $p21^{ras}$, P210 product of bcr/abl rearrangement); mutated tumor-suppressor gene products (e.g., p53); reactivated embryonic gene products not expressed in adult tissues (e.g., P91A found in the P815 mastocytoma); MAGE 1 (found in melanomas and human breast tumors); tissue specific self-antigens expressed by tumors (e.g., tyrosinase); and a variety of others. (Pardoll, D., *Immunol. Today* 14:310–316[1993]). Further, most tumor cell populations express certain common TAAs, but are heterogeneous with respect to the spectrum of TAAs that they express. It is possible that the complete spectrum of tumor associated T-cell epitopes in a given tumor may eventually be identified. However, despite the array of tumor-associated T-cell epitopes expressed in tumors, tumor cells remain poorly immunogenic.

Recent studies have shown that when the killing of cells by the immune system does occur that it is mediated by cytotoxic T-lymphocytes (CTLs). However, the recognition of tumor-associated antigens is restricted by class 1 determinants specified by the major histocompatibility complex. (DeGiovanni, et al., *Int. J. Cancer* 48:270 (1991); Porgador, et al., *J. Immunogenet.* 16:291 (1989); Kim, et al., *Cancer Immunol. Immunother.* 38:185–193 [1994])). Suppression or failure to express MHC class I antigens is one of several documented mechanisms which enable tumor cells to escape T-cell mediated host immunity. (Elliot, et al., *Adv. Cancer Res.* 53:181 (1990); and Tanaka, et al., *Ann. Rev. Immunol.*6:359 (1988)).

Recently there has been a great deal of activity directed toward augmenting the immune response to tumor-associated antigens using cytokines. This strategy attempts to alter the local immunological environment of the tumor cell so as to enhance the presentation of T-cell epitopes or to enhance the activation of tumor-specific T-lymphocytes. (Pardoll, D. *Immunol. Today* 14:310–316 [1993]).

Many cytokine genes have been introduced into tumor cells to produce vaccines having varying degrees of effect on both tumorigenicity and immunogenicity. For example, tumor cells have been modified with genes for interleukin-2 (IL-2)(Porgador, A., et al., *Int. J. Cancer* 53:471-477 [1993]); interferon-α, (IFN-α)(Porgador, A., et al., *Int. Immunol* 150:1458–1570 [1993]); granulocyte-macrophage colony stimulating factor (GM-CSF) (Dranoff, G., et al., *Proc. Nat. Acad. Sci. USA* 90:3539–3543 [1993]) and several others.

Immunizations with neoplastic cells modified to secrete IL-2 (Porgador, et al., *Int. J. Cancer* 53:471–477 (1993), Karp, et al., *J. Immunol* 150:896–908 (1993)), IFN-α (Porgador et al., *J. Immunol* 150:1458–1470 (1993)), or GM-CSF (Dranoff, et al., *Proc. Natl. Acad. Sci. USA* 90:3539–3543 (1993)), among others (Pardoll, et al., *Curr. Opin. Immunol* 4:619–623 (1992), Rosenberg, et al., *J. Clin. Oncol.* 10: 180–199 (1992)), resulted in the generation of CTLs with specificity toward both the cytokine-secreting and non-secreting tumor cells. Experimental animals and a small number of patients with established neoplasms treated with the cytokine-secreting cells survived for prolonged periods, although in most instances tumor-growth eventually recurred.

Because of the important role of the MHC in the presentation of T-cell epitopes on the surface of tumors, attempts have been made to modify expression of the MHC complex in order to improve the immunogenicity of tumor cells. Enhanced expression of MHC class I antigens following exposure of cells to cytokines or transfection of cells with genes specifying MHC class I antigens have been shown to render the treated cells more susceptible to lysis by CTLs. (Weber, J. S., et al., *Cancer Res.* 48:5818 [1988]); Zoller, M. *Int. J. Cancer* 41:256 [1988]); Porgador, A., et al., *J. Immunogenet.* 16:291 [1989]).

Kim, T. S. et al. have shown that when certain specific tumor antigens are expressed in allogeneic cells, that the cells stimulate an improved T-cell response to the specific antigens expressed by the allogeneic cells. (*Int. J. Cancer* 55:865–872 [1993]; and Kim, T. S. et al., *Int J. Cancer* 51:283–289 [1992]). However, the system described by Kim et al. involved the selection of a subset of cells expressing a very limited array of tumor-associated antigens. The use of this subset of cells as a vaccine suffers from the disadvantage that they express only a small proportion of the total array of tumor-antigens that may be expressed in any given tumor. Thus, it is likely that the immune system will recognize only the antigens expressed by the vaccine and thereby select for the survival of those tumor cells expressing other antigens.

In light of the forgoing, there remains a need for tumor-vaccines which evoke an immune response against the array of tumor-associated antigens that may be expressed in any given time.

SUMMARY OF THE INVENTION

The present invention is directed to a method for the treatment of neoplastic disease comprising administering to a mammal having a tumor a cellular immunogen comprising an allogeneic population of cells expressing one or more cytokines and tumor associated antigens encoded by autologous genomic tumor DNA.

The invention is also directed to the above-described method wherein the one or more cytokines is capable of augmenting a T-cell response. The cytokine is selected from the group consisting of interferon α, interferon-γ, the interleukins 1–12, tumor necrosis factor, granulocyte macrophage colony stimulating factor, granulocyte colony stimulating factor and other cytokines capable of augmenting a T-cell response.

The allogeneic cell population may express endogenous cytokine genes or they may be genetically modified to express the one or more cytokine. Tumors comprehended by the method of the present invention include but are not limited to melanoma, lymphoma, plasmocytoma, sarcoma, leukemia, carcinomas, such as renal cell carcinoma, lung carcinoma, breast carcinoma, colon carcinoma, prostate carcinoma and others. The method of the present invention is applicable to the treatment of neoplastic disease in humans and in non-human mammals.

The invention is also directed to a cellular immunogen comprising an allogeneic population of cells expressing one or more cytokine, and tumor-associated antigens encoded by autologous genomic tumor DNA.

Another aspect of the invention is a cellular immunogen produced by the process of providing an allogeneic population of cells which expresses a cytokine encoded by an endogenous cytokine gene or which is encoded by a foreign cytokine gene introduced into the allogeneic cells; introducing into the allogeneic cells genomic DNA derived from a portion of a tumor to be treated whereby at least a portion of allogeneic cells express, one or more tumor associated antigens encoded by the tumor DNA.

Still another aspect of the invention is a pharmaceutical composition useful in the treatment of neoplastic disease comprising the cellular immunogen of the present invention and a pharmaceutically acceptable carrier, diluent or adjuvant.

The invention is also directed to a medicament useful in a method for treating neoplastic disease, the medicament comprising the cellular immunogens of the present invention.

DETAILED DESCRIPTION

The present invention is directed to an immunotherapeutic strategy for the treatment of neoplastic disease and to materials useful in implementing that strategy. The strategy is based on the likelihood that several if not many genes specifying tumor-associated antigens (TAA) have undergone rearrangement in tumor cells and/or on populations of cells comprising a tumor. Further, allogeneic cells of when transfected with genomic DNA derived from a portion of tumor to be treated or from another similar tumor, will result in a population of cells at least some of which will express one or more of the TAAs in the context of the MHC. Expression of the TAAs in the context of the MHC thus allows the presentation of T-cell specific epitopes in such a way as to provoke or augment a cytotoxic T-cell response to the TAAs. The strategy is further based on the ability of cytokines such as interleukin-2 (IL-2), when produced by the transfected cells to further augment the T-cell response by causing an expansion of the T-cell population that recognizes the tumor-associated T-cell epitopes expressed on the transfected cells.

The approach of modifying a cell-line expressing defined allogeneic MHC class I determinants (rather than modification of the tumor cells themselves) was selected for two, complementary reasons. Tumors developed in C57BL/6 mice injected with (non-irradiated) IL-2-secreting B16 cells. Neoplastic cells recovered from the tumors were not IL-2-secreting and, unlike the cells first injected, the proviral insert specifying the IL-2gene was absent (Kim, et al., Int.J. Cancer 55:865–872 (1993)). Thus, these cells were deemed inappropriate for use in implementing the strategy of the present invention. In contrast, tumors were not observed in immunocompetent mice injected with non irradiated IL-2-secreting or non-secreting cells that expressed allogeneic determinants. Like other allografts, the cells were eventually rejected by the immunocompetent recipients. Furthermore, allogeneic antigens expressed by cells chosen to receive the tumor DNA acted synergistically with the TAA in generating the cellular anti-tumor response.

In prior studies, it was found that anti-tumor immunity failed to develop in C3H mice (H-2$^k$ immunized with LM cells (H-2 $^k$) genetically modified to express TAA, under circumstances in which strong responses developed in mice with b, s or d haplotypes immunized with the same cell-type (Kim, et al., Int.J. Cancer 51:283–289 (1992)). Thus, the co-expression of allogeneic antigens by the cellular immunogen provided a second level of protection against the proliferation of the cells in the recipient as it augmented the anti-tumor response. The secretion of IL-2by the cell construct further amplified the anti-tumor response in the immunized mice.

Two non-exclusive mechanisms may explain the improved response against autologous tumor in mice immunized with the IL-2-secreting allogeneic transfected cells. The first is that large numbers of cytotoxic T-lymphocytes (CTLs) with specificity toward tumor associated antigens expressed by the neoplasm are generated in the micro environment of allograft recognition and rejection. The immunogenic properties of tumor cells transfected with genes specifying allogeneic determinants supports this explanation (Hui, K. M., et al., J. Immunol. 143:3835–3843, (1989); and Ostrand-Rosenberg, et al. Int. J. Cancer . 6(Suppl.): 61–68 (1991).

The second is that allogeneic MHC class I determinants present tumor associated T-cell epitopes directly to CTL precursors. The high, local environment of IL-2, secreted by the genetically modified cells, further augments the generation of large numbers of CTLs with anti-tumor specificity.

Lyt-2.2$^+$(CD8$^+$) anti-tumor CTLs were predominant in mice immunized with cells transfected with genomic DNA from the tumor cells. natural killer/lympholine activated killer cells (NK/LAK) cells were the predominant anti-tumor cell-type in mice immunized with cells transfected with DNA from MOPC-315 cells, or cells modified for IL-2-secretion alone. It is likely that the activation of NK/LAK cells reflected the secretion of IL-2 by the modified cells. It was found previously that Lyt-2.2$^+$ cells were the predominant anti-tumor cell-type in C57BL/6 mice immunized with non-IL-2-secreting LM cells that were selected for the expression of TAA, and that NK/LAK cells were predominant in mice injected with TAA-non expressing cells modified to secrete IL-2alone. (Kim, T. S. et al., J. Immunother. 14:298–304, [1993]) Thus, the expression of TAA by LM-IL-2 cells transfected with genomic DNA from the tumor cells may have been responsible for the activation of anti-tumor Lyt-2.2$^+$ T-lymphocytes (CD8$^+$).

In order to implement the immunotherapeutic strategy of the present invention, the plasmid pZipNeoSVIL-2containing the gene for interleukin-2 (IL-2) along with a neo$^4$ gene (which confers resistance to G418) was introduced into LM cells, a mouse fibroblast cell line of C3H origin expressing defined MHC class I antigens (H-2$^k$). After initial selection in growth medium containing G418, IL-2-secretion was confirmed and the cells were then co-transfected with genomic DNA from B16F1 or B16F10 melanoma cells along with DNA from a plasmid (pHyg) that confers resistance to hygromycin. After a second round of selection in growth medium containing sufficient quantities of hygromycin to kill one hundred percent of non-transfected cells, but without further modification, the unfractionated population of transfected cells was tested for its immunotherapeutic properties in C57BL/6 mice (H-2$^b$) with established B16 melanomas (H-2$^b$). Animals with melanomas treated with either of the transfected cell-populations survived significantly (p<0.01) longer than untreated mice, or mice treated with irradiated (5000 rads) B16F1 melanoma cells. The animals also survived longer (p<0.05) than mice with melanoma treated with IL-2-secreting LM cells transfected with genomic DNA from MOPC-315 cells, a non-immunologically cross-reactive murine tumor. As determined by the capacity of monoclonal antibodies to T cell-subsets to inhibit the anti-melanoma response in a $^{51}$Cr-release assay, the anti-melanoma immunity in mice immunized with cells transfected with genomic DNA from either B16F1 or B16F10 cells was mediated primarily by Lyt-2.2$^+$ (CD8$^+$) T-cells.

These results show that cellular immunogens may be prepared by transfecting allogeneic cells modified to express a cytokine capable of augmenting a T-cell response with genomic DNA taken from a portion of tumor or tumor cells derived directly from a patient. The patient may then be treated with the cellular immunogen to induce tumor regression.

EXAMPLE 1

Preparation Of IL-2-Secreting LM (H-2$^k$) Cells

IL-2-secreting LM cells were prepared by transfecting the IL-2gene into the cells using the vector pZipNeoSVIL-2 (Yamada, et al., *EMBO J.* 6:2705–2709 (1987)) using cationic liposomes (Felgner, et al., *Proc. Natl. Acad. Sci. USA* 84:7413–7417 (1987)). The plasmid vector comprises the human IL-2gene and the neo$^r$ gene, both under control of the Moloney leukemia virus long terminal repeat. The neo$^r$ gene confers resistance to the aminoglycoside antibiotic, G418 (Colbere-Garapin, et al., *J. Mol. Biol.* 150:114 (1981)). The gene may also be transduced into cells via virus particles, by transfecting pZipNeoSVIL-2into a viral replication-defective packaging cell line. (Markowitz, et al., *Virol* 167:400–406(1988)).

For use as controls, LM cells were transfected with the plasmid pZipNeoSV(X). Like pZipNeoSVIL-2, pZipNeoSV (X) comprises the Neo$^r$ gene under the transcriptional control of the Maloney leukemia virus long terminal repeat, but lacks the gene for IL-2. This plasmid may also be packaged in a viral replication-defective packaging cell line.

Transfected cells were maintained for 14 days in growth medium containing 1 mg/ml G418 (G418-growth medium). One hundred percent of non-transfected LM cells maintained in G418-growth medium died within this period. Colonies of cells proliferating in the selection medium were pooled for assay of IL-2-secretion and later, additional modification. Every third transfer, the IL-2-secreting LM cells (LM-IL-2) were routinely passaged in growth medium containing 300 mg/ml G418 to eliminate cells that had lost the Neo$^r$ gene (and, by inference, the IL-2gene).

IL-2-secretion by the G418 -resistant cells was assayed using the IL-2-dependent cell-line, CTLL-2 as described in Gillis, et al., *J. Immunol.* 120:2027–2032 (1978). IL-2-dependent CTLL-2 cells were maintained in RPMI-1640 medium supplemented with 10% FBS, 2 mM glutamine, 0.5 mM sodium pyruvate, 15 mM HEPES, 5×10$^{-2}$ mM 2-mercaptoethanol and 100 units/ml IL-2(Genzyme, Cambridge, Mass.). One unit of IL-2gave half-maximal proliferation of CTLL-2 cells under these conditions. The results of these assays are shown in Table 1.

TABLE 1

Secretion OF IL-2 BY Cells Transfected with pZipNeoSVIL-2 Carrying the IL-2 Gene

| | IL-2-secretion (units/10$^6$ cells/48 hrs) | |
|---|---|---|
| Cell-type | Original assay | Subsequent assay (>6 months) |
| LM-IL-2 | 10,000 | 9,500 |
| LM-ZipNeo | 0 | 0 |

The values shown in Table 1 represent the mean from three different experiments. The results show that 1×10$^6$ LM-IL-2 cells produce about 10,000 units/10$^6$ cells when assayed over 48 hours and that IL-2expression in these cells was stable even after 6 months of continuous culture. Further, cells transfected with pZipNeoSV(x) produced no detectable IL-2.

EXAMPLE 2

Detection of mRNAs Specifying IL-2 by Reverse Transcription-Polymerase Chain Reaction (RT-PCR)

The RT-PCR was used as a further test of the expression of the IL-2-gene by LM-IL-2 cells. Total cellular RNA was prepared from LM-IL-2cells and from LM cells transfected with pZipNeoSV(X) according to the method described by Chomczynski and Sacchi (Chomczynski, et al., *Anal. Biochem.* 162:156–159 (1987)). The RNA samples were transcribed into cDNA in a reverse transcription reaction mixture containing 50 mM Tris-HCl (pH 8.3), 75 mM KCl, 3 mM MgCl$_2$, 10 mM dithiothreitol, 0.5 mM each of deoxynucleotide triphosphate (dATP, dTTP, dGTP, and dCTP), 1 unit/ml RNase inhibitor, 2.5 units/μl Moloney murine leukemia virus reverse transcriptase (MMLV-RT) (Gibco BRL, Grand Island, N.Y.) and 0.03μg/ml oligodeoxythymidylateprimer (Gibco BRL). RT-PCR amplification of cDNA was performed in a reaction mixture consisting of 0.4 mM of each specific primer for the IL-2 or the Neo$^r$gene (Clontech Lab., Palo Alto, Calif.), 3–5 μl of the cDNA sample, 1.5 mM MgCl$_2$, and 2.0 U Taq polymerase (Gibco BRL). The Neo specific primers were:

5'GCTGTGCTCGACGTTGTCAC 3'      (SEQ ID NO: 1);

and

5'CTCGGAGTCCAGAGCATCCTG 3'     (SEQ ID NO:2)

Amplification was carried-out for 38 cycles of 94° C. (1 min), 55° C. (1 min), 72° C. (1 min) for the Neo cDNA amplification.

The IL-2 specific primers used for the detection of IL-2 specific transcripts were;

5'ATGTACAGGATGCAACTCCTGTCTT 3'    (SEQ ID NO: 3);

and

5'GTCAGTGTTGAGATGATGCTTTGAC 3'    (SEQ ID NO:4).

Amplification of the IL-2 cDNA was carried out for 32 cycles of 94° C. (45 sec), 60° C. (45 sec), 72° C. (2 min) using a Perkin-Elmer Cetus thermal-cycler.

After amplification, 5 µl of the reaction mixture was removed and analyzed by electrophoresis in a 2.0% agarose gel in TBE buffer, followed by staining of the gel with ethidium bromide. The results indicated the presence of IL-2 specific mRNA and Neo$^r$ specific mRNA in the transfected cells as shown by the presence of a 458 base-pair IL-2 specific amplification product and a 249 bp Neo$^r$ specific amplification product.

EXAMPLE 3

Detection of the IL-2-Gene by Southern Blotting.

Genomic DNA from LM-IL-2 cells was prepared as described by Wigler, et al., *Cell* 14:725–731(1978). Southern blot analysis was performed using this DNA to confirm the integration of the IL-2-gene into the transfected cell genome, as described previously (Russell, et al., *Int. J. Cancer* 47:244–251(1991); and Sambrook, et al., *Molecular Cloning; A Laboratory Manual, Cold Spring Harbor Laboratory*, N.Y. (1992)). $^{32}$P-labeled cDNA encoding human IL-2derived from pZipNeoSVIL-2was used as a probe. The probe was labeled using methods described in Sambrook, et al., *Molecular Cloning; A Laboratory Manual, Cold Spring Harbor Laboratory*, N.Y. (1992). This analysis revealed that two copies of the IL-2gene were integrated into the DNAs of the transfected cells

EXAMPLE 4

Co-Transfection Of LM-2 Cells With Genomic DNA From Tumor Cells And With pHYG In order to produce the cellular immunogens of the present invention, high molecular weight genomic DNA was isolated from each of three progressively growing tumors, B16F1 melanoma, B16F10 melanoma and MOPC-315 plasmocytoma, using techniques described previously (Wigler, et al., *Cell* 14:725–731 (1978)). The cationic liposome-mediated transfection method (Lipofectin®, Gibco BRL) (Felgner, et al., *Proc. Natl. Acad. Sci. USA* 84:7413–7417 (1987)) was used to co-transfect LM-IL-2 cells (1×10$^7$ cells) with genomic DNA (20 µg) from either of the melanoma cell-lines, or from MOPC-315 cells, with DNA (1 µg) from the plasmid pHyg following the supplier's protocol.

The plasmid pHyg carries an *E. coli* gene encoding a hygromycin B phosphotransferase (Sugden, et al., Mol. Cell. Biol. 5:410 (1985)). As an additional control, other LM-IL-2 cells were transfected with DNA (1 µg) from pHyg alone. Other selectable markers such as the herpes simplex thymidine kinase gene may be used to co-transfect with genomic DNA. The choice of a selectable marker will depend on the specific cell line to be transfected and may be readily determined by those of ordinary skill in the art. After transfection the cells were maintained for 14 days in growth medium containing 400 µg/ml hygromycin. The surviving colonies (more than 10$^4$) were pooled and used in the experiments described below. One hundred percent of non transfected LM-IL-2 cells maintained in the hygromycin-growth medium died within this period. IL-2-secreting LM cells (LM-IL-2) transfected with genomic DNA from B16F1 (LM-IL-2/B16F1), 2 /B16F10 (LM-IL2/B16F10), or MOPC-315 (LM-IL-2/MOPC-315 ) cells, secreted approximately the same amount of IL-2as LM-IL-2 cells when tested using the method described in Example 1.

EXAMPLE 5

Survival Of Mice With B16 Melanoma Treated With LM-IL-2 Cells Transfected With Genomic DNA From B16 Cells (Cellular Immunogens)

B16F1 (H-2$^b$) is a highly malignant cell-line derived from a melanoma occurring spontaneously in a C57BL/6 mouse (H-2$^b$). The B16F1 cell line is available from the American Type Culture Collection, Rockville, Md. under ATCC accession no. 6323. B16F10 is a derivative of B16F10 selected for its metastatic properties. Both cell-lines, were maintained by serial passage in histocompatible C57BL/6 mice (Jackson Labs., Bar Harbor, Me.) or at 37° C. in a humidified 7% CO$_2$/air mixture in Dulbecco's modified Eagle's medium containing 10% fetal bovine serum (FBS) and antibiotics (growth medium) (Gibco BRL, Grand Island, N.Y.). MOPC-315 cells (H-2$^d$), a mineral oil-induced plasmacytoma of BALB/c mouse origin (H-2$^d$) (ATCC accession no. TIV23) were maintained by serial passage in BALB/c mice. LM cells (H-2$^k$) were obtained from the American Type Culture Collection, Rockville, Md. (ATCC accession no. CCL1-3). The cell-lines were maintained at 37° C. in a humidified 7% CO$_2$/air atmosphere in growth medium.

Eight to 12 week old pathogen-free C57BL/6 mice (Jackson Labs., Bar Harbor, Me.), highly susceptible to the growth of passively transferred B16 melanoma (minimum lethal dose=5×10$^2$ cells), were used in all experiments. The animals were maintained and treated according to NIH Guidelines for the Care and Use of Laboratory Animals.

In the experiment, naive C57BL/6 mice were injected subcutaneously (sc) with 5×10$^3$ viable B16F1 cells. Six days later, the mice received the first of three injections at weekly intervals of 4×10$^6$ LM-IL-2/B16F1 cells or LM-IL-2/B16F10 cells in a volume of 0.1–0.3 ml in growth medium. Other mice with melanoma were treated with equal numbers of LMIL-2/MOPC-315 with LM-IL-2 cells transfected with DNA from pHyg alone (LM-IL-2/Hyg), with irradiated melanoma cells irradiated with 5000 rads of radiation from a $^{60}$Co source or the mice were not injected. At the time of the first injection of the IL-2-secreting cells, the tumor was less than 2 mm in diameter. Life table methods and log rank analyses were used to determine the statistical differences between the proportion of mice surviving following the different treatments.

Figure 1:
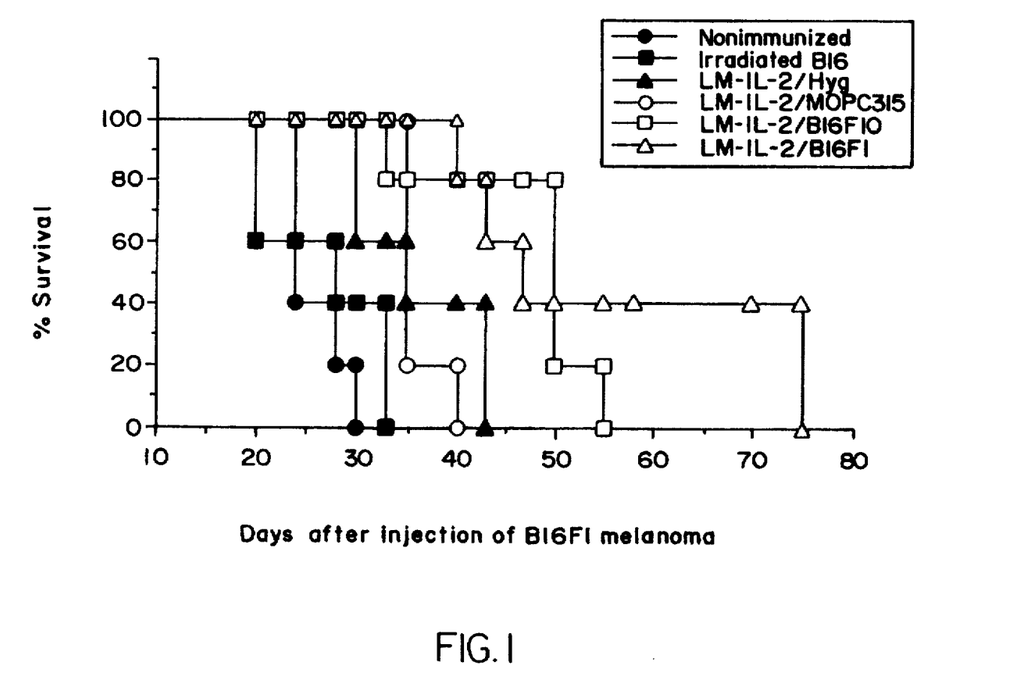
FIG. 1 is a graph showing the survival curves for mice bearing B16F1 melanoma treated with irradiated B16F1 cells (solid squares), LM-IL-2/Hyg (solid triangles), LM-IL-2/MOPC-315 (open circles), LM-IL-2/B16F10 (open squares), and LM-IL-2/B16F1 (open triangles), or untreated mice (solid circles).

The results shown in FIG. 1 indicate that mice with melanoma treated with LM-IL-2/B16F1 cells had a median survival time (MST) of 55.0 days while those treated with LM-IL-2/B16F10 cells had an MST of 46.4 days. MSTs for both treated groups were significantly longer (P<0.05) than mice with melanoma treated with cells from any of the various control groups. The median survival of untreated mice injected with B16F1 cells alone was 26 days. Treatment with irradiated B16F1 cells failed to prolong the survival of mice with melanoma. The differences in survival of untreated mice with melanoma, or mice with melanoma treated with irradiated B16 cells or LM-IL-2/MOPC-315 cells were not significant. A cellular immunogen expressing IL-2and IFN$_\gamma$ along with tumor antigens also increased the MST in melanoma bearing mice.

In addition the injections themselves caused no harm. Neoplasms were not detected in tumor-free mice injected with viable IL-2-secreting transfected LM cells. Like other allografts, the cells were rejected over a period of two to three weeks.

EXAMPLE 6

Spleen Cell-Mediated Cytotoxicity Against B16F1 Melanoma Cells Mononuclear cells from the spleens of C57BL/6 mice immunized with the various cellular immunogens described above were used as sources of effector cells for cytotoxicity determinations. C57BL/6 mice (at least 2 per group) were injected subcutaneously (s.c.) and intraperitoneally (i.p.) respectively with 2×10 LM-IL-2/B16F1 or LM-IL-2/B16F10 cells at each injection site. Two weeks later, spleen cell suspensions were prepared by forcing the mouse spleens through 40 gauge stainless steel screens in 5 ml of growth medium and transferred to 15 ml centrifuge tubes (Sarstedt, Newton, N.C.). Large clumps of cells and debris were allowed to settle for 1 min and the cells remaining in the supernatant were collected, overlaid onto a Ficoll/Hypaque gradient (Pharmacia, Piscataway, N.J.) and centrifuged (2,000 rpm) for 25 min at room temperature. The viability of the mononuclear cells at this point was greater than 98%, as determined by trypan blue dye exclusion (0.4% trypan blue).

Aliquots of the cell suspensions were co-incubated in growth medium at 37° C. for 5 days with mitomycin C-treated (Sigma Chemical Co., St Louis, MO) (50 µg/ml for 45 min at 37° C.) cells of the same type as used to immunize the mice. After incubation, the population that failed to adhere to the plastic cell culture flasks was collected and used as the effector cells for the cytotoxicity determinations against B16F1 melanoma cells.

Spleen cell-mediated cytotoxicity measurements against B16 cells were performed in a standard $^{51}$Cr-release assay. Briefly, 5×10 B16F1 cells were labeled with $^{51}$Cr during a 1 hr incubation at 37° C. in growth medium containing 100 mCi of sodium $^{51}$Cr (Amersham, Arlington Heights, Ill.). After three washes with Dulbecco's modified Eagle's medium, 1×10$^4$ $^{51}$Cr-labeled B16 cells were incubated for 4 hrs at 37° C. with the nonplastic-adherent population of spleen cells from the immunized mice (prepared as described above), at effector cell:target cell ratios (E:T) of 100:1 and 200:1. Afterwards, the percent specific cytolysis was calculated as:

$$\frac{\text{Experimental }^{51}\text{Cr release} - \text{Spontaneous }^{51}\text{Cr release}}{\text{Maximum }^{51}\text{Cr release} - \text{Spontaneous }^{51}\text{Cr release}} \times 100$$

TABLE 2

CTYOTOXICITY TOWARD MELANOMA IN POPULATIONS OF SPLEEN CELLS FROM MICE IMMUNIZED WITH LM-IL-2/B16F1 CELLS

| Effector cells Immunized with: | Treatment | % Cytolysis at E:T ratios of 100:1 | 200:1 |
|---|---|---|---|
| LM-IL-2/B16F1 | — | 29.1 ± 2.1 | 31.2 ± 1.2$^c$ |
| | anti-Lyt2.2$^+$ | 9.2 ± 1.4 | 13.1 ± 0.5$^d$ |
| | anit-asialo G$_{M1}$ | 23.8 ± 0.7 | 19.4 ± 2.3$^d$ |
| LM-IL-2/B16F10 | — | 27.7 ± 1.4 | 25.0 ± 4.2$^c$ |
| | anti-Lyt2.2$^+$ | 12.4 ± 1.3 | 14.7 ± 0.4$^d$ |
| | anti-asialo G$_{M1}$ | 20.6 ± 0.4 | 17.8 ± 1.0 |
| LM-IL-2/MOPC-315 | — | 12.1 ± 0.6 | 10.9 ± 1.0$^e$ |
| | anti-Lyt2.2$^+$ | 11.5 ± 0.4 | 14.1 ± 1.4 |
| | anti asialo G$_{M1}$ | 3.1 ± 0.6 | 2.4 ± 1.5 |
| LM-IL-2/Hyg | — | 20.1 ± 0.5 | 18.3 ± 0.7$^e$ |
| | anti-Lyt2.2$^+$ | 19.6 ± 1.3 | 22.6 ± 2.2 |
| | anti-asialo G$_{M1}$ | 8.0 ± 0.7 | 2.3 ± 1.1$^d$ |
| Irradiated B16F1 | — | 4.8 ± 0.4 | 6.5 ± 0.8 |
| | anti-lyt2.2$^+$ | 0.4 ± 1.1 | 6.2 ± 0.6 |
| Non-immunized | anti-asialo G$_{M1}$ | –0.7 ± 2.8 | 3.6 ± 0.2 |
| | — | 0.0 ± 4.2 | 2.4 ± 0.7 |
| | anti-Lyt2.2$^+$ | –1.8 ± 3.7 | 2.4 ± 5.2 |
| | anti-asialo G$_{M1}$ | –1.9 ± 0.1 | –0.2 ± 2.3 |

The Student's t test was used to determine the statistical differences between cytotoxic activities in mice in various experimental and control groups. A p value of less than 0.05 was considered significant.

The results are shown in Table 2 and indicate that the specific cytolysis toward the melanoma cells was significantly (p<0.001) higher in spleen cell-populations from mice immunized with LM-IL-2/B16F1 cells and from mice immunized with LM-IL-2/B16F10 than in spleen cell populations from non-immunized mice. An anti-melanoma response was also detected in mononuclear cell-populations from the spleens of mice immunized with IL-2-secreting LM cells transfected with genomic DNA from MOPC-315 cells, and in a population of cells from mice immunized with IL-2-secreting LM cells transfected with DNA from the plasmid pHyg alone. However, the magnitude of these responses was clearly less than that present in mice immunized with LM-IL-2/B16F1 or LM-IL-2/B16F10 cells.

EXAMPLE 7

Determination of the Classes of Effector Cells Activated for Anti-Melanoma Cytotoxicity in Mice Immunized With Cellular Imunogens The effect of anti-Lyt-2.2$^+$ monoclonal antibodies (mAbs) (directed to Lyt-2.2$^+$ CD8$^+$ T-cells) or anti-asialo G$_{M1}$ mAbs (directed to NK/LAK cells) on the spleen cell-mediated cytotoxicity reactions described above was used to identify the predominant cell-types activated for anti-melanoma cytotoxicity in mice immunized with the cellular immunogens described above (Fearon, et al., Cell 60:397–403 (1990)). After the five day period of incubation, the nonplastic-adherent cells were incubated at 4° C. for 1 hr with excess quantities of the mAbs [anti-Lyt-2.2$^+$ (CD8$^+$): hybridoma 3.155 (Sarmiento, et al., J. Immunol. 125:2665–2672 (1985)) or anti-asialo G$_{M1}$ (Kasai, et al., Eur. J. Immunol. 10:175–180 (1980)) (Wako Chemical Co., Dallas, Tex.)] before the $^{51}$Cr-release assay was performed. The antibodies were titered such that the concentrations used were 5 times the amount required to saturate the binding of the specific cell-types from naive C57BL/6 mice, as determined by cytofluorometric analyses of serially diluted antibodies.

As shown in Table 2 above, treatment of spleen cells from mice immunized with LM-IL-2/B16F1 or LM-IL-2/B16F10 cells with either anti-Lyt-2.2$^+$ or anti-asialo G$_{M1}$ mAbs alone was insufficient to completely eliminate the anti-melanoma response. A mixture of both mAbs was required to reduce the response to "background", that is, the level present in a population of non- antibody-treated spleen cells from naive C57BL/6 mice. In an analogous study, following immunization with an IL-2-secreting cellular immunogen, treatment of a spleen cell-population with anti-L3T4 mAbs directed to T-helper cells had no significant effect on the anti-melanoma response.

An analogous approach was used to determine the cell-types activated for anti-melanoma immunity in mice injected with LM-IL-2/MOPC-315 LM cells and in mice immunized with IL-2-secreting cells transfected with pHyg alone. As indicated in Table 2, in both instances anti-asialo Gm mAbs alone reduced the cytolytic activity to "background". Anti-Lyt-2.2$^+$ mAbs had no significant effect upon the anti-melanoma activity (Table 2).

Thus, immunization of mice susceptible to the growth of melanoma with an unfractionated population of IL-2-secreting cells transfected with genomic DNA from either of two melanoma cell-lines induced specific anti-melanoma immune responses that were capable of prolonging the survival of mice with melanoma. The immunity was mediated primarily by Lyt-2.2$^+$ T cells and, to a lesser extent, NK/LAK cells.

EXAMPLE 9

Survival of Mice Bearing B16 Melanoma or C1498 Lymphoma Treated with Various Modified Cellular Immunogens Experiments were conducted to examine the effect of various cellular immunogens on the median survival time of mice bearing either C1498 lymphoma or B16 melanoma.

The cellular immunogens were produced by transfecting LM-IL-2 cells produced as described in Example 1, C1498 lymphoma cells (ATCC Accession No. TIV49), or J558 myeloma cells (ATCC Accession No. TIV6) using the method described in Example 2. The cellular immunogens produced were designated LM IL-2/C1409 and LM IL-2/J558 (expressing IL-2 and J558 tumor-associated antigens). In addition, the LM IL-2/B16F cellular immunogens produced in Example 2 were used in these studies.

C57BL/6 mice (5 per group) were subcutaneously injected with $5 \times 10^3$ melanoma cells or with $1 \times 10^5$ C1498 cells. At the same time, mice receiving tumor cells also received the first of three weekly subcutaneous injections of $4 \times 10^6$ cells of one of the cellular immunogens shown in Table 3.

Animals receiving B16 melanoma cells were treated with LM IL-2/B16, LIL-2/C 1498, LM IL-2/J558, or LM IL-2 cellular immunogens. Control animals with B16 melanoma received no treatment. Animals receiving C1498 lymphoma cells were treated with LM IL-2/B16 or LM IL-2/C1498 cells. Control animals with C1498 lymphoma received no treatment.

Figure 2A:
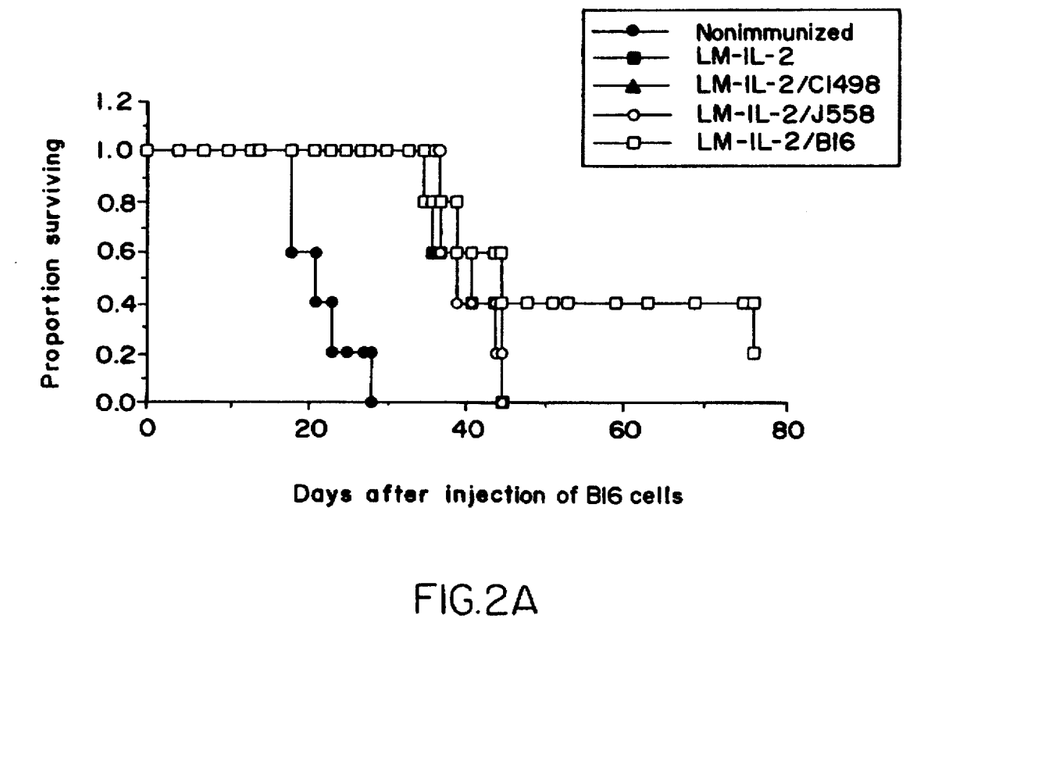
FIG. 2A is a graph showing the survival curves for mice bearing B16F1 melanoma treated with LM-IL-2 cells (solid squares), LM-IL-2/C1498 cells (solid triangles), LM-IL-2/J558 cells (open circles), LM-IL-2/B16F1 cells (open squares), or untreated mice (solid circles).
Figure 2B:
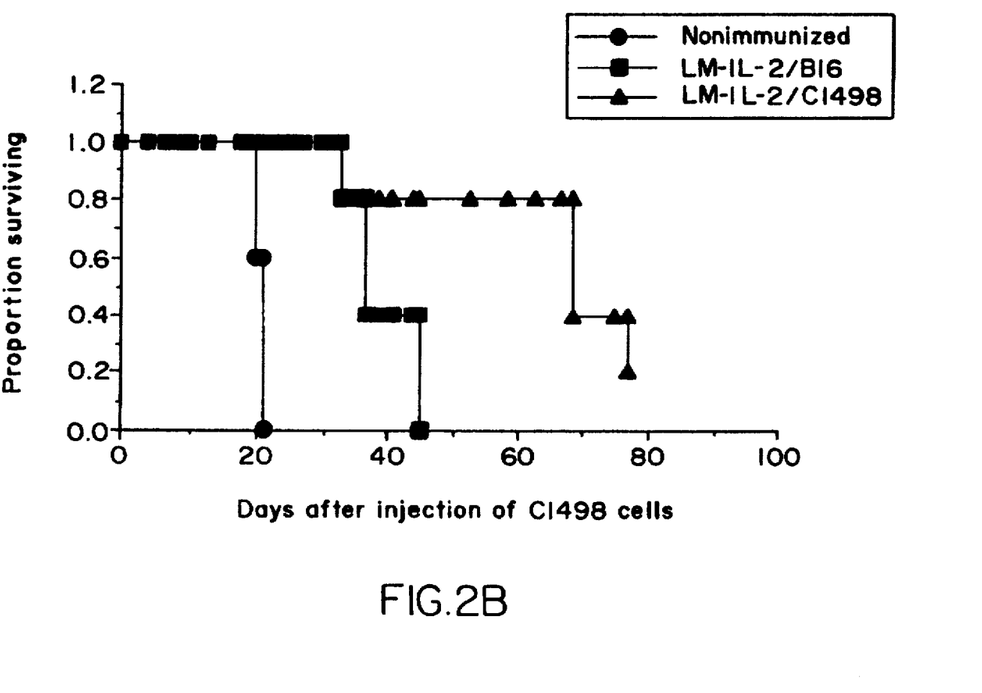
FIG. 2B is a graph showing the survival curves for mice bearing C1498 lymphoma treated with LM-IL-2/B16F1 cells (solid squares), LM-IL-2/C1498 cells (solid triangles), and untreated mice (solid circles).

The results of these experiments are summarized in Table 3 and FIG. 2.

TABLE 3

SPECIFICITY OF THE ANTI-TUMOR RESPONSE

| TUMOR CELLS | CELLULAR IMMUNOGEN | MEDIAN SURVIVAL TIME (DAYS) |
| --- | --- | --- |
| B16F1 | non-immunized | 21.6 ± 3.7 |
| C1498 | non-immunized | 20.6 ± 0.49 |
| B16F1 | LM IL-2/B16F1 | 60.0 ± 20.9 |
| B16F1 | LM IL-2/C1498 | 41.4 ± 4.98 |
| B16F1 | LM IL-2/J558 | 40.4 ± 3.85 |
| B16 | LM IL-2 | 40.4 ± 4.77 |
| C1498 | LM IL-2/B16 | 39.4 ± 5.37 |
| C1498 | LM IL-2/C1498 | 62.0 ± 19.70 |

As shown in Table 3, and FIG. 2, control mice receiving B16 melanoma cells or C1498 lymphoma cells with no treatment had a medium survival time of 21.6±3.7 days and 20.6±0.49 days respectively.

The cellular immunogens yielding the greatest increases in median survival time were those that were prepared with genomic DNA taken from cells corresponding to those which gave rise to the tumors (autologous tumor cell DNA), i.e. LM IL-2/B16 constructs extended the median survival time the most in animals with B16 melanoma while LM IL-2/C1498 increased the median survival time the most in animals with C1498 lymphoma. However, significant increases in median survival time were seen in all animals receiving any allogeneic cell constructs including the LM IL-2 construct which had not been transfected with genomic DNA from any tumor. These results suggest that while allogeneic cells modified to express cytokine (IL-2) are themselves capable of enhancing an animal's immune response to a tumor, the effect is markedly enhanced by the expression of analogous tumor-associated antigens.

EXAMPLE 10

Spleen-Cell Mediated Immunity Toward B16 Melanoma and C1498 lymphoma

The $^{51}$Cr-release assay described in Example 6 was used to detect spleen-cell mediated immunity (cytotoxicity) toward B16 melanoma and C1498 lymphoma.

Tumors were established in naive C57BL/6 mice by subcutaneously injecting either $5 \times 10^3$ B16 melanoma cells or $1 \times 10^5$ C1498 lymphoma cells. The mice receiving the B16 melanoma cells were each treated with $4 \times 10^6$ LM IL-2/B16, LM IL-2/C1498, LM IL-2/J558, LM IL-2cells simultaneously with the administration of the cellular immunogens followed by two more treatments with the cellular immunogens at 7 day intervals. One group of control mice receiving B16 cells were left untreated.

Mice receiving C1498 lymphoma cells were each treated with $4 \times 10^6$ LM IL-2/B16 or with LM IL-2/C1498 cells as described in Example 5. One group of control mice receiving C1498 cells were left untreated. Seven days after the last injection, mononuclear cells were obtained from the spleens of mice in each group as described in Example 6. Spleen cells were then incubated for 7 days with mitomycin-C treated cellular immunogens of the same cell type used for immunization. The spleen cells were then tested for their capacity to lyse $^{51}$Cr-labeled B16 melanoma cells, or C1498 lymphoma cells as described in Example 6.

The involvement of NK/LAK cells in the cell mediated response was also tested by adding an excess of monoclonal antibodies specific for NK/LAK cells to the spleen-cell suspension prior to their use in the 5$^1$Cr-release assay. The results of these assays are shown in Table 4.

TABLE 4

ANTI-TUMOR CYTOTOXICITY FROM MICE IMMUNIZED WITH CELLULAR IMMUNOGENS

| TARGET CELLS | EFFECTOR CELLS (Immunization) | % CYTOLYSIS AT 100:1 RATIO | % CYTOLYSIS AT 100:1 E:T RATIO (PLUS ANTI-NK/LAK Ab) |
| --- | --- | --- | --- |
| B16 | None | 0.47 ± 1.11 | 5.60 ± 1.74 |
| B16 | LM IL-2/B16 | 36.18 ± 5.16 | 37.25 ± 0.06 |
| B16 | LM IL-2/C1498 | 12.59 ± 1.60 | 6.33 ± 1.60 |
| B16 | LM IL-2/J558 | 17.35 ± 0.55 | 7.39 ± 2.03 |
| B16 | LM IL-2 | 18.43 ± 4.11 | 9.31 ± 2.67 |
| C1498 | None | −10.38 ± 2.03 | −0.68 ± 7.31 |

TABLE 4-continued

ANTI-TUMOR CYTOTOXICITY FROM MICE IMMUNIZED
WITH CELLULAR IMMUNOGENS

| TARGET CELLS | EFFECTOR CELLS (Immunization) | % CYTOLYSIS AT 100:1 RATIO | % CYTOLYSIS AT 100:1 E:T RATIO (PLUS ANTI-NK/LAK Ab) |
|---|---|---|---|
| C1498 | LM IL-2/C1498 | 31.16 ± 3.16 | 46.03 ± 5.20 |
| C1498 | LM IL-2/B16 | 11.45 ± 3.28 | 10.91 ± 1.48 |

The results of these assays show that cytolysis of tumor cells was greatest toward a given tumor when the cellular immunogen used for immunization had been transfected with autologous tumor DNA. However, significant cytolysis was also seen using spleen cells from animals receiving cellular immunogens that had been transfected with heterologous tumor DNA although it was significantly lower than with cells containing autologous tumor DNA.

Results also shown that cytolysis by spleen-cells derived from mice immunized with LM-IL-2/B16 cells or LM-IL-2/C1498 cells was not inhibited by anti-NK/LAK antibody, and thus immunity was not mediated by NK/LAK cells.

EXAMPLE 11

Preparation Of Individualized Cellular Immunogens

The foregoing examples illustrate that it is possible to prepare individualized cellular immunogens directed to a specific tumor which will extend the median survival time of patients with that specific tumor. Such individualized cellular immunogens will be useful either alone or in combination with other treatment modalities for the treatment of neoplastic disease. This approach will be useful in treating not only melanoma but also most if not all other tumor types including but not limited to lymphomas, sarcomas, carcinomas, plasmocytomas, leukemias, and tumors of nervous system origins.

The preparation of individualized cellular immunogens entails preparing a modified allogeneic cell line having a MHC type (or HLA type) which is foreign to the patient. Such a cell type is exemplified above by LM cells (H-$2^k$). Exemplary human cell lines whose HLA type has already been determined include human melanoma cell lines available from the ATCC under accession numbers HTB70, HTB63 and HTB71.

Exemplary modifications include the introduction of a vector containing an expressible cDNA encoding a cytoline such as IL-2, INF-$\gamma$ granulocyte-colony stimulating factor (Colombo, M.P. et al., *J. Exp. Med.* 173: 889–847 [1991]); interferon α (IFNα) (Ferrantini, M., et al. *Cancer Res.* 53: 1107–1112 [1993]); interleukin-6 (IL-6) (Porgador, et al., *Cancer Res.* 52: 3679–3686 [1992]); tumor necrosis factor (TNF) (Blankenstein, et al. *J. Exp. Med.* 173: 1047–1052 [1991]); and interleukin-4 (Golvrobeck, P. T., et al. *Science* 254: 713–716 [1991]) GM-CSF (Dranoff, G., et al., *Proc.* *Nat. Acad. Sci. USA* 90:3539–3543 [1993]) or other cytokines capable of augmenting an anti-tumor response to a tumor antigen. Such a vector is exemplified by pZipNeoSVIL-2in Example 2 described above. However, allogeneic cells lines expressing endogenous cytokines may also be used. Once a modified allogeneic cell line is established and is shown to produce the cytokine or cytokines of interest (the combination of IL-2 and INF-$\gamma$ is preferred), then this cell line is used as a target for further modification by introducing isolated purified genomic DNA taken from a patient's own tumor. Tumor samples are obtained during surgery, by needle aspiration, or by other well-known methods. Genomic DNA is then isolated and purified from the tumor sample directly using methods well known in the art including those set out in Sambrook, et al., Molecular Cloning: A Laboratory Manual, Cold Spring Harbor Laboratory N.Y. (1992). Tumor samples may also be grown in culture using methods well known in the art in order to increase the amount of DNA available for transfection or to select for a particular sub-population of tumor cells from which to isolate DNA.

Isolated purified DNA from the tumor or tumor cells is then transfected into a population of the modified allogeneic cells along with a selectable marker such as pHyg or any of a number of other selectable markers. Genomic DNA may be transfected into the modified allogeneic cells using any of a number of methods including the use of cationic liposomes as described in Example 4, by calcium-phosphate co-precipitation, by electroporation or by any of a number of other well known methods for introducing genomic DNA into cells. Transfected cells are then grown under selection pressure to kill 100% of the cells that fail to express the selectable marker. Those cells surviving selection are then pooled to provide a tumor-associated antigens which will serve to stimulate a T-cell mediated immune response. As illustrated in Examples 5 and 9, such T-cell responses have been shown to increase the MST of animals bearing autologous tumors. Although the number of modified, transfected cells used to treat a patient may vary, a preferred dosage range is from about $1 \times 10^3$ to about $5 \times 10^9$ cells per injection. The cellular immunogen may administered as a live vaccine or the immunogen may be modified by irradiation, chemical treatment or other means known in the art so as to render the cellular immunogen incapable of proliferation.

The subcutaneous route of injection is preferred but other routes such as the intraperitoneal, intramuscular, or intravenous routes are contemplated by the present invention.

The present invention also permits the preparation of generic cellular immunogens which express one or more cytokines and which express tumor associated antigens encoded by genomic DNA derived from tumors or tumor cells other than the patients own tumor. These generic cellular immunogens are prepared as described above.

The forgoing examples are presented by way of illustration and are not intended to limit the invention as set forth in the appended claims. All of the references cited above are incorporated herein by reference.

I claim:

1. A method for treating a mammal having a tumor, the method comprising administering to said mammal a cellular immunogen, the cellular immunogen comprising an allogerieic population of non-tumor cells transformed with and expressing a DNA sequence encoding a cytokine, said cytokine expressing allogeneic population of cells being further cotransformed with autologous tumor cell entire genomic DNA and a selectable marker, wherein the administration of said cellular immunogen results in the stimulation of a tumor-specific immune response in said mammal.

2. The method of claim 1 wherein the cytokine is capable of augmenting a T-cell response.

3. The method of claim 1 wherein the cytokine is selected from the group consisting of interleukin-1, interleukin-2, interleukin-3, interleukin-4 , interleukin-5, interleukin-6 , interleukin-7, interleukin-8, interleukin-9, interleukin-10, interleukin-11, interleukin-12, interferon α, interferon γ, tumor necrosis factor, granulocyte macrophage colony stimulating factor, and granulocyte colony stimulating factor.

4. The method of claim 1 wherein the tumor is selected from the group consisting of melanoma, lymphoma, plasmocytoma, carcinoma, sarcoma, tumors of the nervous system, and leukemia.

5. The method of claim 1 wherein the tumor is selected from the group consisting of lung carcinoma, renal cell carcinoma, melanoma, breast carcinoma, carcinoma of the prostate and colon carcinoma.

6. The method of claim 1 wherein the mammal is a non-human mammal.

7. The method of claim 1 wherein the mammal is human.

8. The method of claim 1 wherein the cellular immunogen comprises about $1 \times 10^3$ to about $5 \times 10^9$ cells.

9. The method of claim 1 wherein the cellular immunogen is rendered incapable of proliferation.

10. The method of claim 1 wherein the cellular immunogen is administered to said mammal by a route of administration selected from the group consisting of subcutaneous, intraperitoneal, intramuscular, and intravenous routes of administration.

11. A cellular immunogen useful for the treatment of tumors, said cellular immunogen being produced by a process comprising:
   a) transforming an allogeneic population of non-tumor cells with a DNA sequence encoding a cytokine and a first selectable marker, operably linked to a promoter;
   b) selecting cells transformed in step (a) for expression of said cytokine and said selectable marker;
   c) growing cell selected in step (b);
   d) co-transforming the cells of step (c) with autologous tumor cell entire genomic DNA and a second selectable marker operably linked to a promoter;
   e) selecting cells co-transformed in step (d) for expression of said second selectable marker; and
   f) growing said co-transformed cells selected in step (e).

12. The cellular immunogen of claim 11 wherein the autologous tumor genomic DNA is isolated from a tumor selected from the group consisting of melanoma, lymphoma, plasmocytoma, carcinoma, sarcoma, tumors of the nervous system, and leukemia.

13. The cellular immunogen of claim 11 wherein the autologous tumor genomic DNA is isolated from a tumor selected from the group consisting of lung carcinoma, renal cell carcinoma, breast carcinoma, carcinoma of the prostate, and colon carcinoma.

14. A pharmaceutical composition comprising a pharmaceutically acceptable diluent, adjuvant, or carrier and a cellular immunogen produced by a process comprising the steps of:
   a) transforming an allogeneic population of non-tumor cells with a DNA sequence encoding a cytokine and a first selectable marker, operably linked to a promoter;
   b) selecting cells transformed in step (a) for expression of said cytokine and said selectable marker;
   c) growing cell selected in step (b);
   d) co-transforming the cells of step (c) with autologous tumor cell entire genomic DNA and a second selectable marker, operably linked to a promoter;
   e) selecting cells co-transformed in step (d) for expression of said second selectable marker; and
   f) growing said co-transformed cells selected in step (e).

* * * * *

UNITED STATES PATENT AND TRADEMARK OFFICE
CERTIFICATE OF CORRECTION

PATENT NO. : 5,759,535
DATED : June 2, 1998
INVENTOR(S) : Edward P. Cohen

It is certified that error appears in the above-identified patent and that said Letters Patent is hereby corrected as shown below:

Title page,
Item [57], ABSTRACT: After "expressing" delete -- S --

Column 4,
Line 16: "(H-2$^K$" should read -- (H-2$^K$) --
Line 66: "neo$^4$" should read -- neo$^r$ --

Column 5,
Line 22: "$^{81}$Cr" should read -- $^{51}$Cr --

Column 9,
Line 9: "10" should read -- $10^6$ --
Line 33: "10" should read -- $10^6$ --
Line 35: "$^{51}$Cr" should read -- $^{31}$Cr --
Line 49: "CTYOTOXICITY" should read -- CYTOTOXICITY --
Line 62: Table 2: "3.1" should read -- 2.1 --

Column 10,
Line 4: "CTYOTOXICITY" should read -- CYTOTOXICITY --

Column 11,
Line 6: "Gm" should read -- $Gm_1$ --
Line 43: "LIL-2/C" should read -- LM IL-2/C --
Line 54: "ANIT" should read -- ANTI --

Column 13,
Line 50: "cytoline" should read -- cytokine --

UNITED STATES PATENT AND TRADEMARK OFFICE
CERTIFICATE OF CORRECTION

PATENT NO. : 5,759,535
DATED : June 2, 1998
INVENTOR(S) : Edward P. Cohen

It is certified that error appears in the above-identified patent and that said Letters Patent is hereby corrected as shown below:

<u>Column 14,</u>
Line 4: "2in" should read -- 2 in --
Line 8: "2and" should read -- 2 and --
Line 34: "a tumor-associated" should read -- population of cytokine-secreting cells at least a portion of which express tumor-associated.... --

Signed and Sealed this

Eighteenth Day of September, 2001

Attest:

*Nicholas P. Godici*

NICHOLAS P. GODICI
*Attesting Officer*     *Acting Director of the United States Patent and Trademark Office*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:1:

GCTGTGCTCG ACGTTGTCAC         20

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:2:

CTCTTCGTCC AGATCATCCT G         21

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:3:

ATGTACAGGA TGCAACTCCT GTCTT         25

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: DNA     ( x i ) SEQUENCE DESCRIPTION: SEQ ID NO:4:

GTCAGTGTTG AGATGATGCT TTGAC         25